United States Patent [19]

Iwama et al.

[11] Patent Number: 5,383,459
[45] Date of Patent: Jan. 24, 1995

[54] ULTRASONIC THERAPY APPARATUS

[75] Inventors: Nobuyuki Iwama; Kiyoshi Okazaki, both of Tochigi; Yasuhiro Kanaya, Gunma, all of Japan

[73] Assignee: Kabushiki Kaisha Toshiba, Kawasaki, Japan

[21] Appl. No.: 875,786

[22] Filed: Apr. 29, 1992

[30] Foreign Application Priority Data

May 1, 1991 [JP] Japan .................. 3-100160
Nov. 15, 1991 [JP] Japan .................. 3-300292

[51] Int. Cl.[6] ........................... A61B 17/22
[52] U.S. Cl. ............... 128/660.03; 601/3; 601/4
[58] Field of Search ......... 128/24 AA, 24 EL, 660.03

[56] References Cited

U.S. PATENT DOCUMENTS

| 4,984,575 | 1/1991 | Uchiyama et al. | 128/24 EL |
| 5,036,836 | 8/1991 | Terai et al. | 128/24 EL |
| 5,044,354 | 9/1991 | Goldhorn et al. | 128/24 EL |

Primary Examiner—Ruth S. Smith
Attorney, Agent, or Firm—Foley & Lardner

[57] ABSTRACT

An ultrasonic treatment apparatus has an applicator for generating ultrasound for an object to be treated, an ultrasonic probe arranged in the applicator for acquiring tomographic image information of the object to be examined and/or destroyed, and an applicator support for supporting the applicator such that the applicator is movable in several directions. This ultrasonic treatment apparatus further includes a provision for changing an approach direction of the applicator between a downward approach and an upward approach to achieve suitable treatment of the object to be treated, a monitor for displaying the tomographic image information of the object supplied from the ultrasonic probe, and an approach direction indicator for indicating a condition of the approach direction of the applicator, whether in the downward approach or in the upward approach on the monitor.

2 Claims, 12 Drawing Sheets

ULTRASONIC THERAPY APPARATUS

BACKGROUND OF THE INVENTION

1. Field of the Invention

The present invention relates to an improvement of an ultrasonic therapy apparatus for destroying an object, e.g., cancer cells or stones, in a subject to be examined by focused energy of a shock wave, or to perform treatment.

2. Description of the Related Art

A conventional ultrasonic therapy apparatus, for example, an extracorporeal shock wave treatment apparatus, comprises an applicator, an applicator support unit, a couch for providing support to a patient, a shock wave control device, a tomographic imaging display unit, and a water control device, etc. The applicator includes a shock wave transducer which has a plurality of electro-acoustic transducer elements for transmitting a focused shock wave to a predetermined direction and depth in the patient. A transmission side of the applicator is controlled to the patient downwardly, after that, the transmitted shock wave from the shock wave transducer can effectively destroy a kidney stone or gallstone in the patient.

Consequently, in a conventional shock wave treatment apparatus, whereby the applicator is arranged above the patient, transmits the shock wave to the patient downwardly. This arrangement of the applicator is defined as a downward approach type. On the other hand, an applicator arranged below the patient transmits the shock wave to the patient upwardly. This arrangement of the applicator is defined as an upward approach type. An advantage of the upward approach type to the other type is easy operation for coinciding a focus point of the shock wave to a calculus. Namely, the operator can adjust the position of the applicator by virtue of confirmation of the positions of several parameters, e.g., condition and body surface of the patient, position of the applicator, and the contact condition between the patient and the applicator.

Although the upward approach type has the advantage of easy operation for adjusting the focus position against the calculus, the upward approach type also has disadvantages when the therapy object is a gallstone.

When a gallstone is destroyed by the shock wave from the applicator of the upward approach type, the patient lays prone. In the prone posture, the gallstone is positioned under a rib and lung. Hence, the transmitted shock wave is absorbed and attenuated by air in the lungs. And in the shock wave therapy apparatus using a ultrasonic imaging probe positioned in the center of the applicator, the structure under the lung is not displayed on the ultrasonic tomographic image, because the ultrasonic beam from the imaging probe is also absorbed and attenuated by air in the lungs. Further, the gallstone is moved by patient movement, based on breath, etc., hence the above operation for coinciding the focus to the gallstone is very difficult.

Furthermore, when the applicator using the downward approach is contacted with the patient, the distance between the applicator and a kidney stone in the patient is approximately 5 cm to 12 cm, and the distance between the applicator and the gallstone in the patient is approximately 2 cm to 7 cm. As is well known in ultrasonic technology, the attenuation coefficient of tissue varies with depth of the object. The attenuation coefficient of tissue increases substantially linearly with frequency, with the high frequency spectral components of a returned signal being attenuated more severely than the low frequency components. Typically, the center frequency of the received signal drops in frequency with the depth of penetration.

Such problem is related to the shock wave treatment apparatus in hyperthermia, with the upward approach applicator type also having the same problem.

SUMMARY OF THE INVENTION

The present invention has been conceived in consideration of the above situation, and has as its object to provide an ultrasonic therapy by applying the focus point of the shock wave to the object to be destroyed.

In order to achieve the above object, an ultrasonic treatment apparatus has an applicator for generating an ultrasound to an object to be treated, an ultrasonic probe arranged in the applicator for acquiring tomographic image information of the object to be examined and destroyed, and an applicator support means for supporting said applicator movably in several directions, said apparatus also having:

means for changing an approach direction of said applicator between a downward approach and an upward approach against said object in order to achieve suitable treatment of said object to be treated;

monitor means for displaying the tomographic image information of said object supplied from said ultrasonic probe; and approach direction indicating means for indicating a condition of the approach direction of said applicator, whether in a downward approach or an upward approach.

Furthermore, in order to achieve the above object, an ultrasonic treatment apparatus has an applicator for generating an ultrasound to an object to be treated, and an applicator support means for supporting the applicator movably in the X-Y coordinate direction, Z direction, and rotation direction, said apparatus also having:

means for changing an approach direction of the applicator between a downward approach and an upward approach against said object in order to achieve suitable treatment of said object to be treated;

driving motors which are provided to each portion of the applicator support means for displacing the applicator in the X-Y coordinate direction, Z direction, and rotation direction;

an operation panel having several switches and several outputs connected to said switches, said outputs connected to each of said driving motors for energizing each of said driving motors based on the operation of said switches;

approach direction detection means for detecting an approach direction, whether in a downward approach or an upward approach; and means for inverting the driving direction of said driving motors in order to achieve a coincidence between the displacing direction of the applicator support means and the operation direction of said switches on said operation panel, when said upward approach is selected.

Furthermore, in order to achieve the above object, an ultrasonic treatment apparatus has an applicator for generating an ultrasound to an object to be treated, and an applicator support means for supporting the applicator movably in several directions, said apparatus also having:

an ultrasonic probe arranged in the applicator for acquiring tomographic image information of said object to be examined and destroyed, said probe having a construction for selectively emitting high and low frequency ultrasound;

means for changing an approach direction of the applicator between a downward approach and an upward approach against said object in order to achieve suitable treatment of said object to be treated;

monitor means for displaying the tomographic image information of said object supplied from said ultrasonic probe;

and ultrasonic frequency conversion means for converting an emitted ultrasound frequency from said ultrasonic probe, whereby said emitted ultrasound frequency is converted to a low frequency when the upward approach is selected.

With the above structure, the ultrasonic therapy apparatus of the present invention can select the downward approach or upward approach, further one can see these approach directions based on the displayed tomographic image. Accordingly, for example, the downward approach is selected when the object to be treated is a kidney stone, the upward approach is selected when the object to be destroyed is a gallstone, and these approach directions can be confirmed by the displayed tomographic image.

DETAILED DESCRIPTION OF THE PREFERRED EMBODIMENTS

An embodiment of a shock wave treatment apparatus according to the present invention will now be described with reference to the accompanying drawings.

Figure 1:
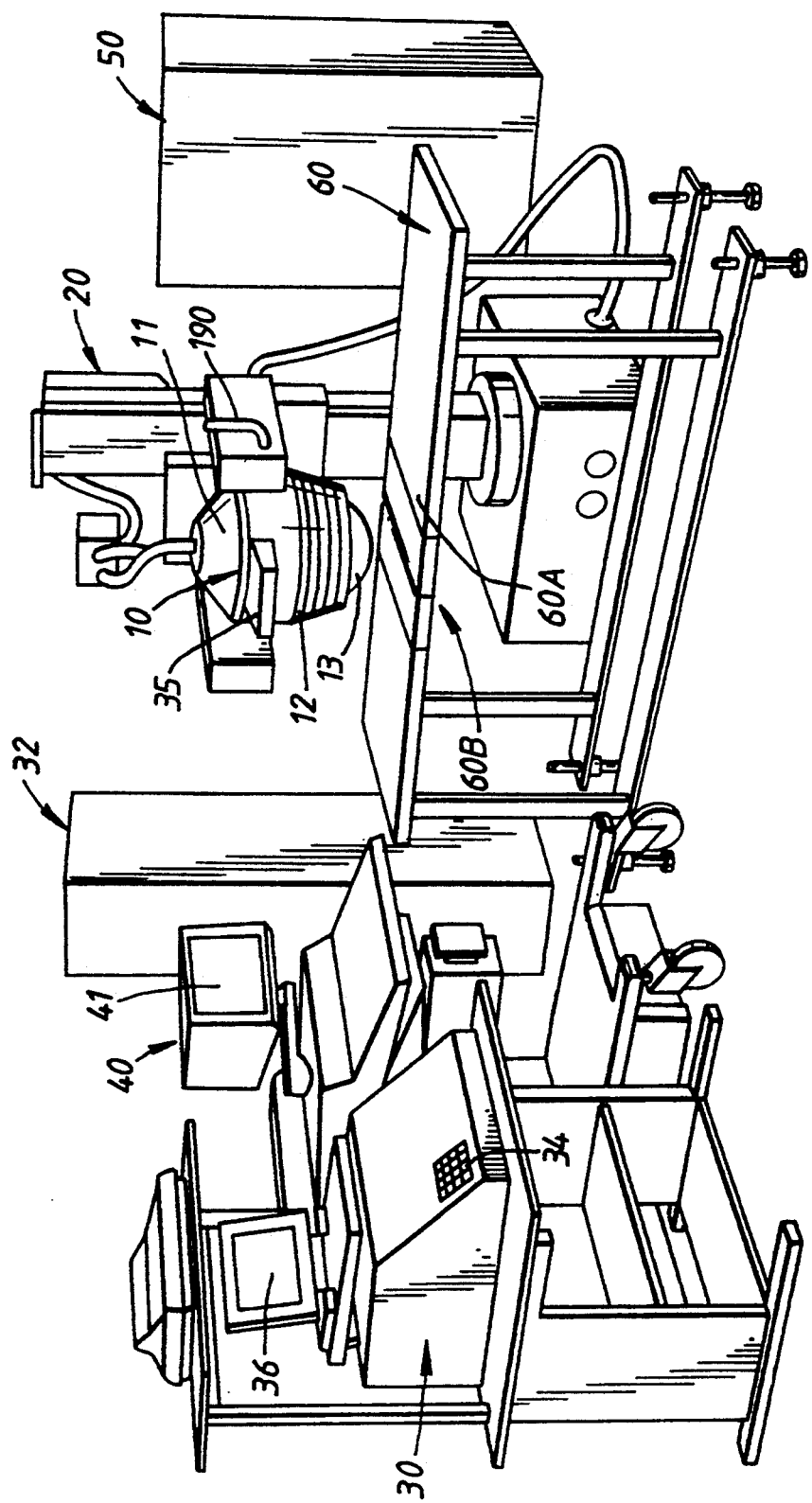
FIG. 1 is a perspective view of an ultrasonic therapy apparatus indicating the downward approach condition according to the present invention.
Figure 3:
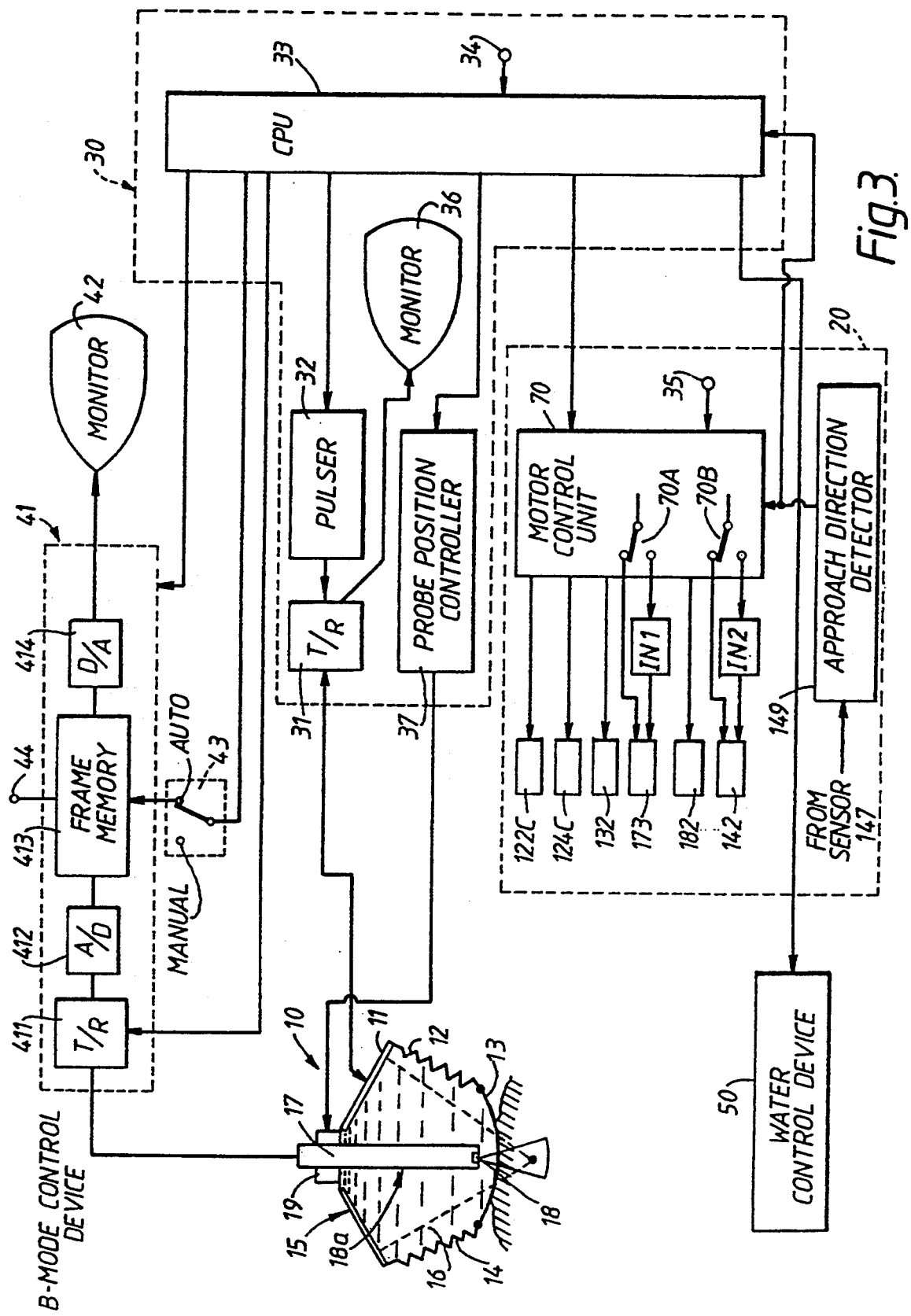
FIG. 3 is a block diagram showing an arrangement of a shock wave treatment apparatus of the present invention.

Referring now to FIG. 1, the shock wave treatment apparatus of the first embodiment consists of an applicator 10, applicator support device 20, shock wave control device 30, ultrasonic tomogram imaging device 40, water control device 50, and couch 60. The applicator 10 comprises a shock wave generator 11 which has a through hole at a center portion, a bellows 12, diaphragm 13, and the applicator 10 forms an airtight construction 14, as seen in FIG. 3. This airtight construction 14 is fixed to a frame 15, and the airtight construction 14 is filled by water 16 as an ultrasound penetration material, as shown in FIG. 3. A rod member 17 is inserted into the airtight construction 14 through the through hole of the frame 15 and the shock wave generator 11. An ultrasonic transducer 18 for observing the tomographic image is arranged in an end of rod member 17, hence an ultrasonic probe 18 a is constructed therefrom. The frame 15 has a probe moving mechanism 19 which allows movement of the ultrasonic probe 18 a within the airtight construction 14 toward a downward and upward direction. The shock wave generator 11 is formed by a plurality of high power type ultrasonic transducers which are arranged in a circular pattern on the frame 15 around the through hole of the frame 15. In this arrangement of the ultrasonic transducer, the transmitted shock wave forms a focus point of a predetermined depth which is determined by the radius of the concave shock wave generator 11.

Referring to FIG. 1, the applicator support device 20 supports the applicator 10 and permits some horizontal movement (XY-axis), large up and down movement (large Z-axis), small up and down movement (small z-axis), turn over, and inclination movement. A detailed explanation of the applicator support device 20 will be set forth later.

Figure 4:
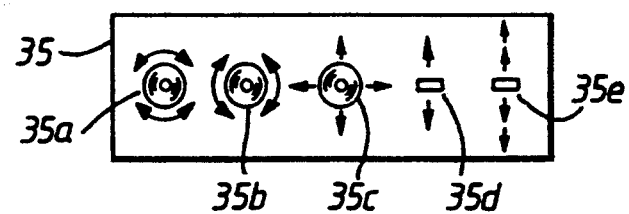
FIG. 4 is a definite plane view of an operation panel shown in FIG. 2.

Referring back to FIG. 3, the shock wave control device 30 consists of an ultrasonic transmitting and receiving unit (T/R) 31, a pulser 32, a central processing unit (CPU) 33, a fixed operation panel 34, an operation panel 35 which can be easily placed on and taken off, a monitor 36, and a probe position controller 37. The T/R 31 functions to supply a high power or low power pulse from the pulser 32 to the shock wave generator 11 selectively. Here, the high power pulse is generated for obtaining the shock wave, and the low power pulse is generated for confirming a condition of coincidence between the focus of shock wave and the calculus. Statistical data obtained such as a number of emissions etc. of the high power and the low power pulses is displayed on the monitor 36. The probe position controller 37 controls the downward/upward movement of the ultrasonic probe 18 a by a control signal from the CPU 33, and sets the ultrasonic probe 18 a to a predetermined position within the airtight construction 14. The operation panel 35 which can be easily put on and taken off is fitted to the frame 15 of the applicator 10. As can be seen in FIG. 4, the operation panel 35 has five operation switches for the movement of the applicator, i.e., a first one 35 a for the inclination movement along the turn over direction, a second one 35 b for the inclination movement along the front and back direction of the applicator 10, a third one 35 c for XY movement along the XY-axis, a fourth one for the small up and down movement along the small z-axis, and a fifth one 35 e for the large up and down movement along the large Z-axis.

Referring back to FIG. 3, the ultrasonic tomogram imaging device 40 comprises a B-mode control device 41 and a monitor 42. More particularly, the B-mode control device 41 consists of a transmission and reception unit (T/R) 411, an A/D converter 412 for converting supplied analog data to digital data, a frame memory 413 for storing the digital data from the A/D 412, and a D/A converter 414 for converting the digital data supplied from the frame memory to analog data. The analog data from the D/A 414 is supplied to the monitor 42, hence a ultrasonic tomographic image is displayed on the monitor 42. Here, an upper and lower movement of stored tomogram data in the frame memory 413 is turned over based on a control signal from CPU 33 via a switching unit 43 or a turn over switch 44 which directs the turn over at a desired time. Also, the switching unit 43 is changed between an AUTO position and a MANUAL position according to an operator switch.

The applicator support device 20 includes a plurality of motors, and circuitry for controlling the motors. As shown in FIG. 3, an output of a motor control unit 70 has two switches 70A and 70B connected to motors 122C, 124C, 132, and 182 directly, and is connected to motors 173 and 142 both directly and via an inverter circuit IN 1 and IN 2, respectively. The switches 70A and 70B can select either the direct connection or the connection via the each inverter circuits IN 1 and IN 2 with the motors 173 and 142, respectively. The switches 70A and 70B can select any terminal based on the output of an approach direction detector 149 which will be described later. The function of the each motor is as follows: the motor 122C displaces the applicator support device 20 along the X-axis direction, the motor 124C displaces the applicator support device 20 along the Y-axis direction, the motor 132 moves the applicator 10 along the Z-axis direction, the motor 173 moves the applicator 10 along the z-axis direction, the motor 182 is used for inclining the applicator 10, and the motor 142 is used for rotating the applicator 10.

The water control device 50 controls supplying and draining the water 16 within the airtight construction 14 of the applicator 10. According to this water control, a depth of the shock wave focus within the patient is adjusted to a suitable depth for treatment of the calculus. Referring to FIG. 1, a table top 60A is used to carry the patient and has a shutting and opening portion 60B. The shutting and opening portion 60B is opened when the upward approach for shock wave treatment is selected by the operator.

Figure 2:
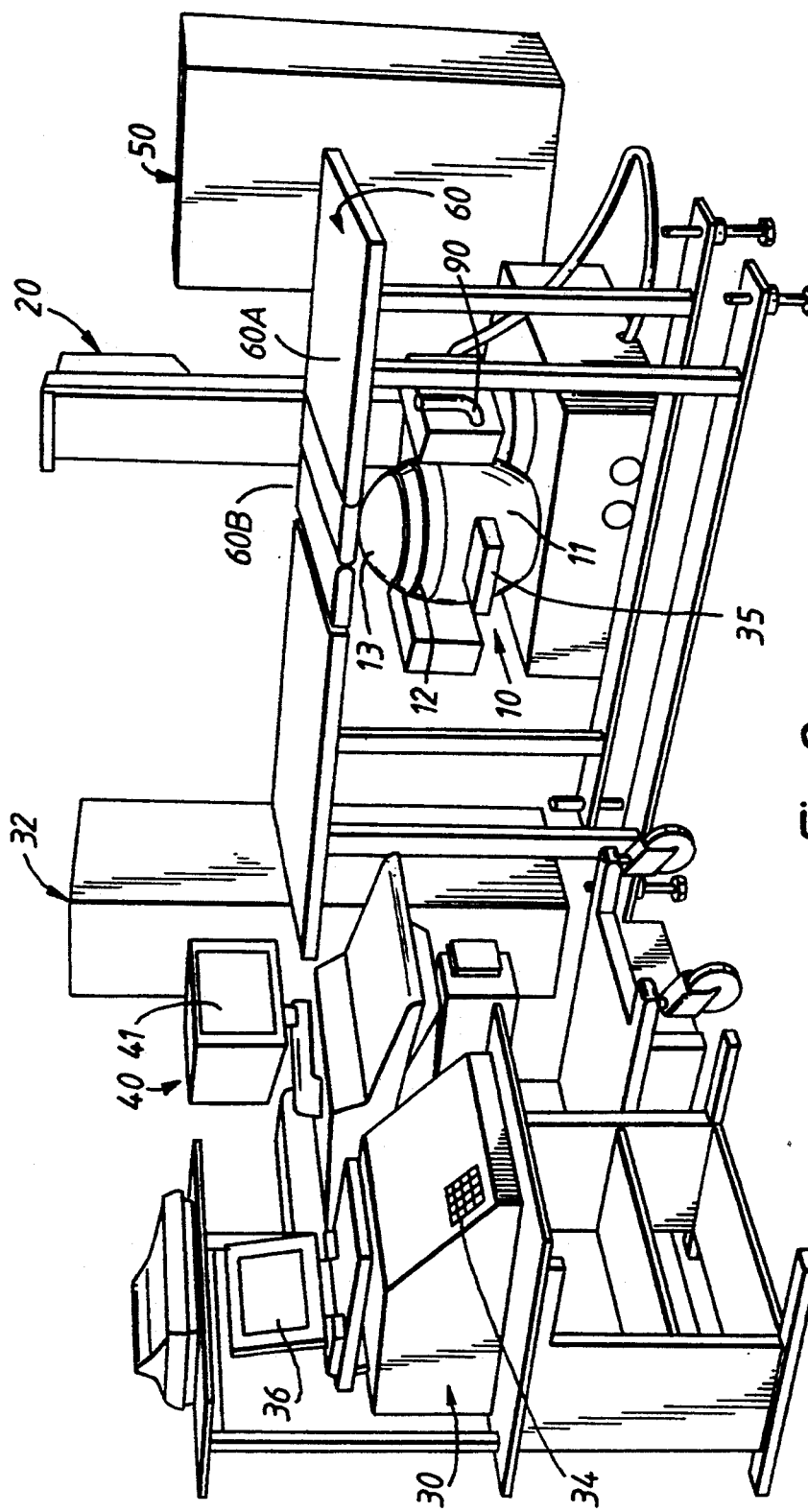
FIG. 2 is a perspective view of an ultrasonic therapy apparatus indicating the upward approach condition according to the present invention.
Figure 5:
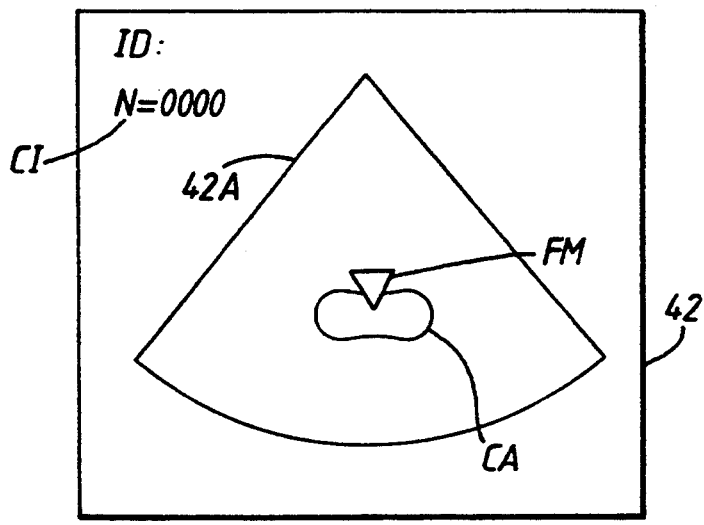
FIG. 5 illustrates a condition of the downward approach displayed on a monitor shown in FIG. 3.
Figure 6:
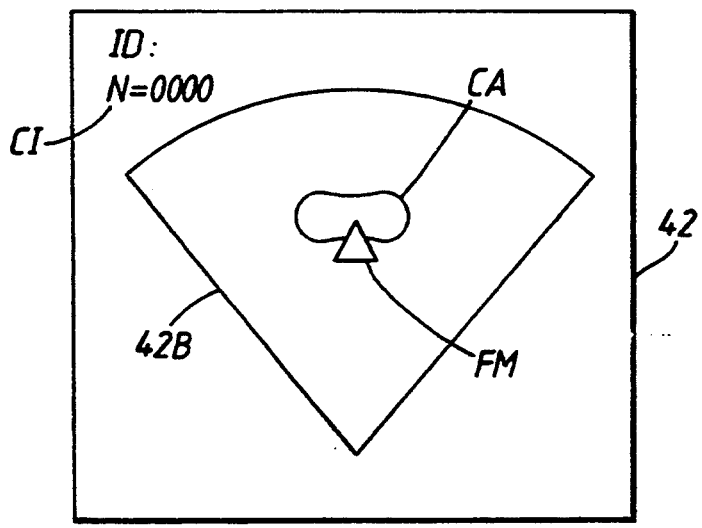
FIG. 6 illustrates a condition of the upward approach displayed on a monitor shown in FIG. 3.

In the above construction, the applicator 10 can be set in a position for downward approach as shown in FIG. 1, and the applicator 10 can be set in a position for upward approach as shown in FIG. 2. This selection of the approach direction is allowed by operation of the applicator support device 20. If the applicator 10 is set for the downward approach, a sector tomographic image 42A is displayed on the monitor 42 with a focus marker FM as shown in FIG. 5, and if the applicator 10 is set for the upward approach, the sector tomographic image 42B is displayed upside down on the monitor 42 with focus marker FM as shown in FIG. 6. Consequently, the approach condition, downward or upward, the focus position of the shock wave, and the position of the calculus can be observed easily. A CI shows character information related to the patient and/or shot No. of shock wave etc., and a CA shows a calculus image.

Figure 7:
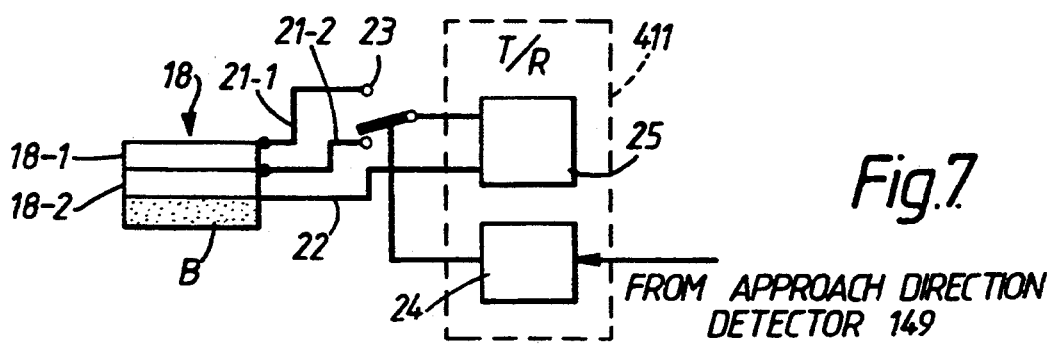
FIG. 7 is a modified ultrasonic imaging system.

Further, the ultrasonic transducer may be modified as shown in FIG. 7, wherein, the ultrasonic transducer 18 consists of two transducers 18-1 and 18-2 on a backing member B. The transducer 18-1 is sandwiched by two electrodes 21-1 and 21-2 for energizing the transducers. And the transducer 18-2 is sandwiched by the electrode 21-2 and a ground 22 which is on the backing member B. The electrodes 21-1 and 21-2 to be connected with pulser 25 are selected by switch 23. The switch 23 is changed by a selector 24 which is controlled by the output of the approach direction detector 149. By way of the above transducer construction, the frequency of the emitted ultrasound may change, namely, the frequency of the emitted ultrasound is certified depending on a thickness of the transducer. Hence, the switch 23 selects one of two frequencies. When both the transducers 18-1 and 18-2 are energized, then the frequency of the emitted ultrasound becomes 3.5 MHz, and when only the transducer 18-2 is energized, then the frequency of the emitted ultrasound becomes 5 MHz. The ultrasound frequency of 3.5 MHz is used when the treatment object is a kidney stone, the ultrasound frequency of 5 MHz is used when the treatment object is a gallstone. Consequently, in the case when the applicator using the downward approach is contacted with the patient, the kidney stone is located in a relatively deep position. Then the ultrasound frequency used is 3.5 MHz, hence the kidney stone located in the deeper position can be observed clearly. For the case when the applicator using the upward approach is contacted with the patient, the gallstone is located in a relatively shallow position. Then the ultrasound frequency used is 5 MHz, hence the gallstone located in a relatively shallow position also can be observed with a high contrast image.

Figure 8:
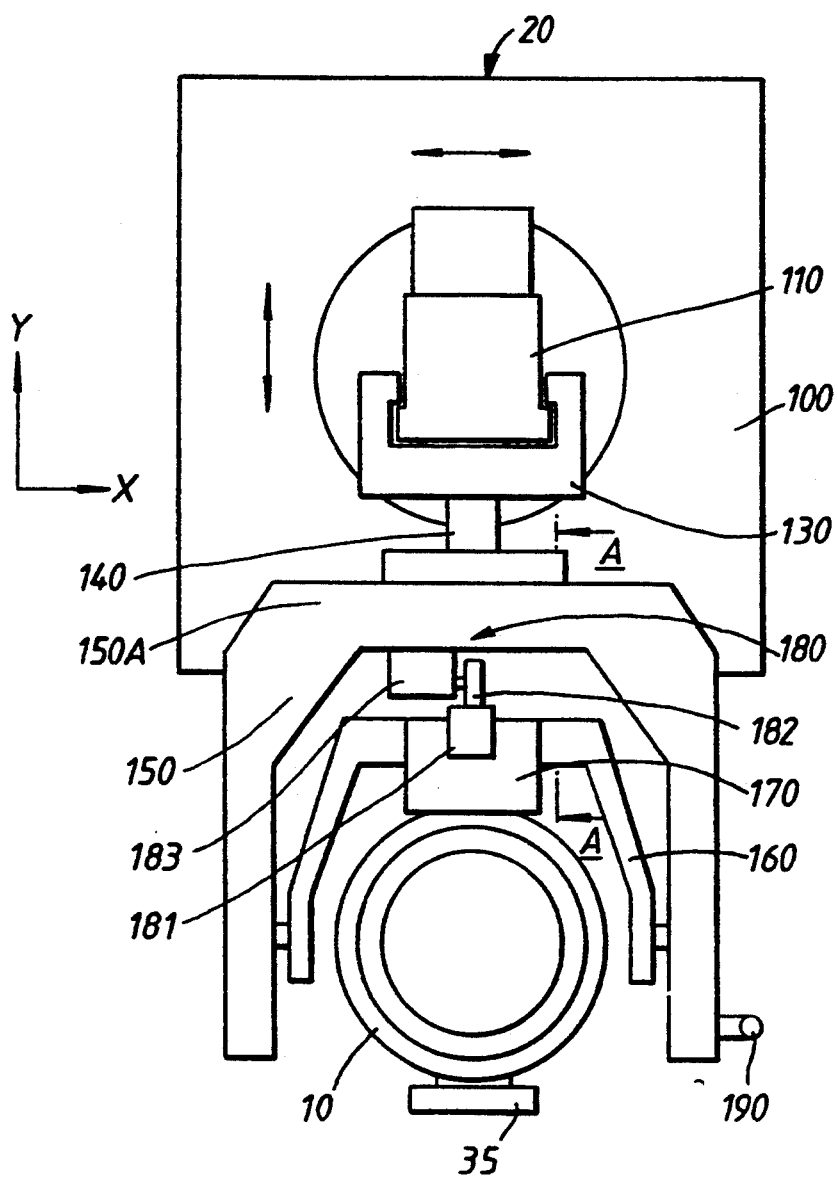
FIG. 8 is a top view, with portions broken away for clarity, of an applicator and an applicator support device shown in FIG. 3.
Figure 9:
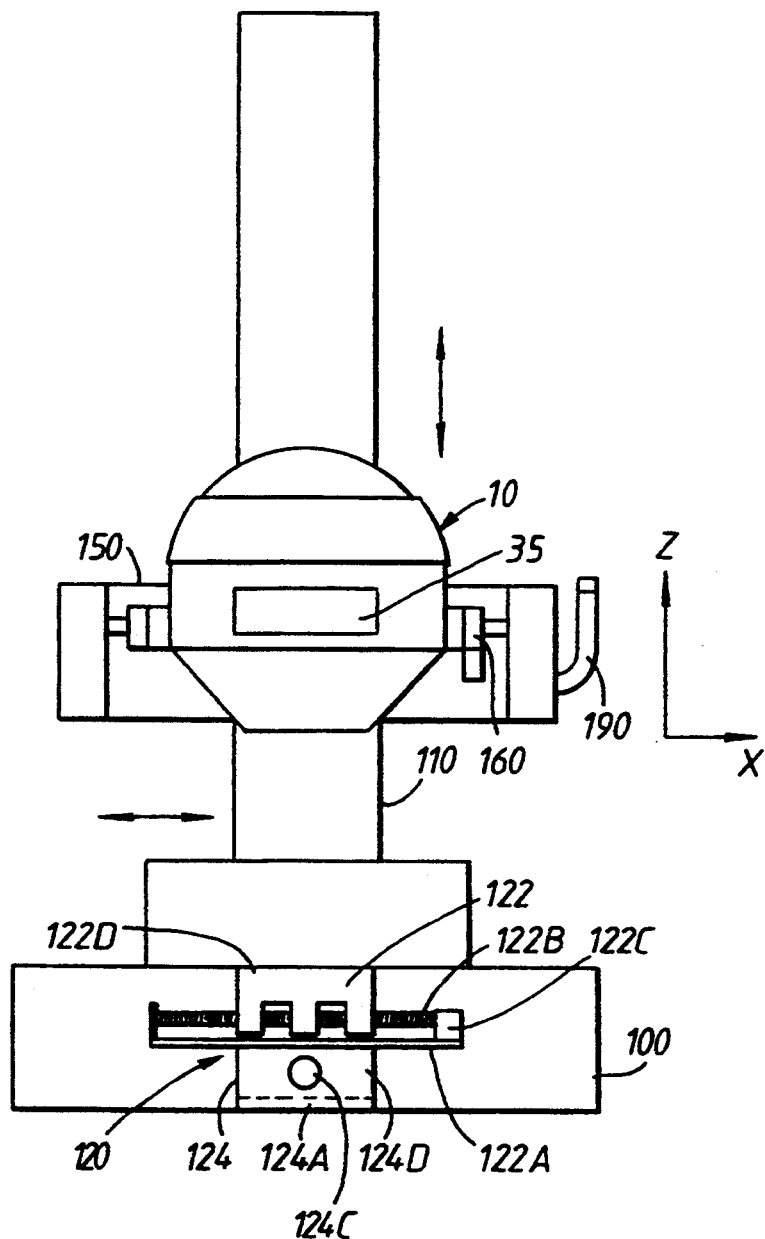
FIG. 9 is a front view of that shown in FIG. 8.
Figure 10:
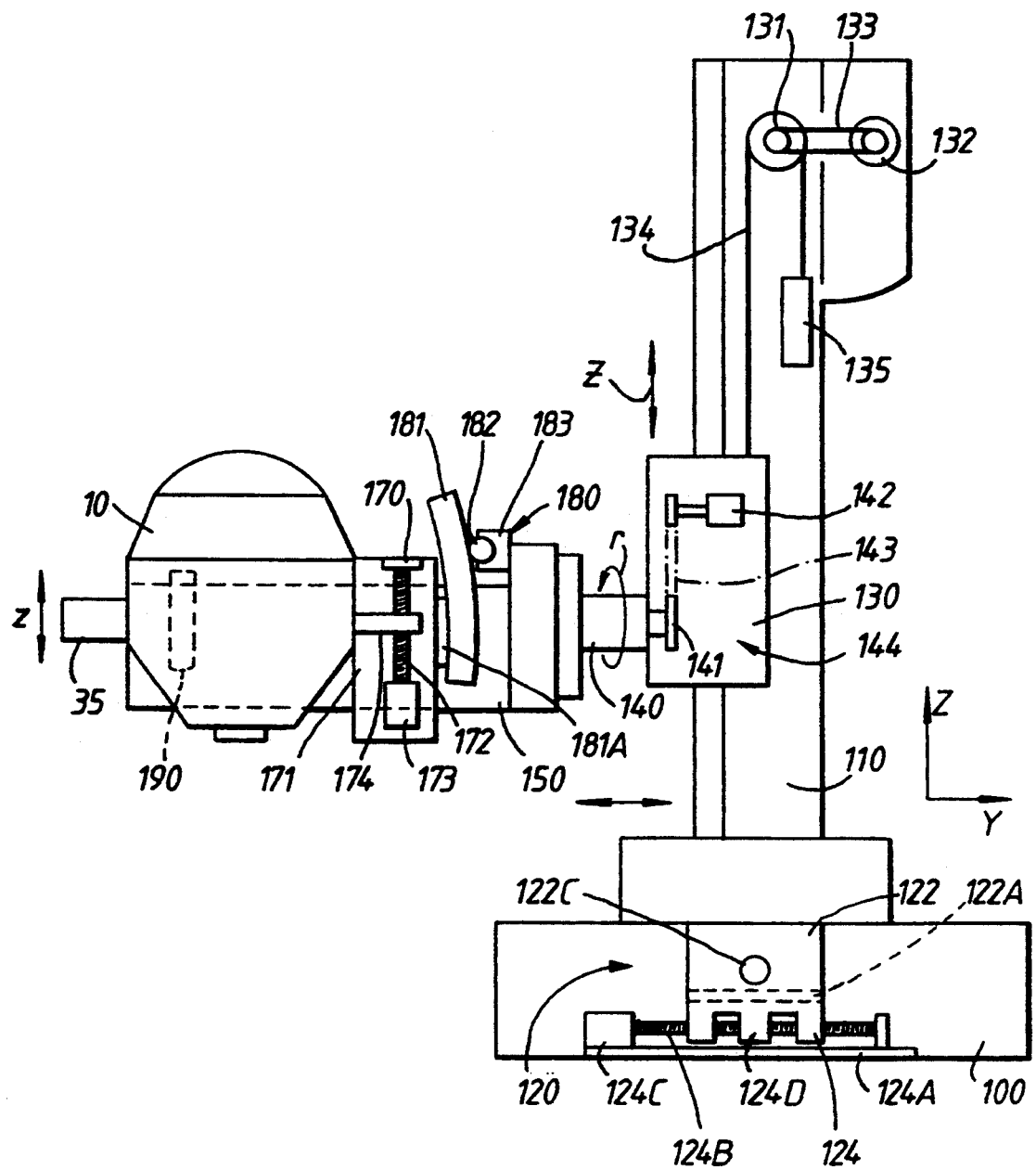
FIG. 10 is a side view of that shown in FIG. 8.

A detailed embodiment of the applicator support device 20 will now be described. As shown in FIG. 8, a base 100 set up on a floor has a tower 110. This tower 110, as shown in FIG. 9 and FIG. 10, is permitted displacement in both the X-axis and Y-axis direction by XY-axis displacement device 120 provided within the base 100. This XY-axis displacement device 120 is constructed with a Y-axis displacement mechanism 124 and an X-axis displacement mechanism 122 as shown in FIG. 9. These displacement mechanisms of the X-axis and the Y-axis are leadscrew mechanisms. As shown in FIG. 9, the X-axis displacement device 122 comprises a rotatable screw 122B provided on an X-axis fixed plate 122A and a screw 122B. The screw 122B is provided for rotation by rotating a motor 122C positioned on an end of the screw 122B. An X-axis lead 122D is engaged with the screw 122B, hence the X-axis lead 122D can be moved along the X-axis direction by driving the motor 122C. And as shown in FIG. 10, the Y-axis displacement device 124 comprises a rotatable screw 124B provided on a Y-axis fixed plate 124A and a screw 124B. The screw 124B is provided for rotation by rotating a motor 124C positioned on an end of the screw 124B. An Y-axis lead 124D is engaged with the screw 124B, hence the Y-axis lead 124D can be moved along the Y-axis direction by driving the motor 124C. The Y-axis fixed plate 124A is fixed to the base 100, and the X-axis fixed plate 122A is coupled to the tower 110. Consequently, the tower 110 can be displayed toward both the X-axis and Y-axis direction individually by means of driving the motor 122C and 124C of the XY-axis displacement device 120.

In FIG. 10, the tower 110 has a C-shaped sliding member 130, and the sliding member 130 can be slid along a Z-axis on the tower 110. This tower 110 also has a sprocket 131 and a motor 132 in an end of the tower 110, and the sprocket 131 and the motor 132 are engaged by a chain 133. The sprocket 131 is also engaged by a wire 134 which connects to the sliding member 130 at one end of the wire 134 and connects to a balance weight 135 at the other end. Hence, when the motor 132 is energized, sliding member 130 is adjusted to a desired position along the Z-axis on the tower 110. In other words, the applicator 10 is permitted to move along the Z-axis direction.

The sliding member 130 has a rotating axis 140 which has a sprocket 141 at one end of the rotating axis 140. The other end of the rotating axis 140 is fixed to a C-shaped arm 150. The sliding member 130 has an arm rotation mechanism 144 which comprises a sprocket 141, motor 142, and chain 143 engaged between the sprocket 141 and motor 142. Hence, by means of energizing the motor 142, the C-shaped arm 150 is permitted to rotate around an arrow r as shown in FIG. 10. In other words, the direction of emission of the shock wave from the applicator 10 can change between the downward approach and the upward approach at a desired timing.

The C-shaped arm 150 has a C-shaped support 160 which connects to the C-shaped arm 150 at an axis 161 provided on both ends of the C-shaped support 160. A mid portion of the C-shaped support 160 is fixed to an applicator support base 170 which supports the applicator 10 slidably to the C-shaped support 160. The applicator support base 170 has a screw mechanism 171 which includes a screw 172, a motor 173 for rotating the screw 172, and a lead 174 engaged with the screw 172. An end portion of the lead 174 is fixed to the applicator 10. Consequently, applicator 10 can be moved along the z-axis by rotating the motor 173.

Figure 11:
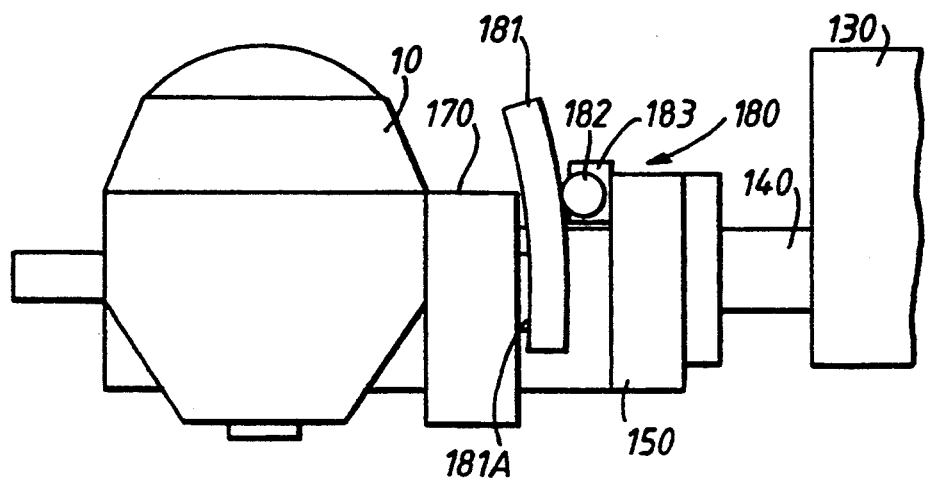
FIGS. 11 to 15 are illustrative diagrams showing an example of the applicator inclination mechanism of FIG. 8.
Figure 12:
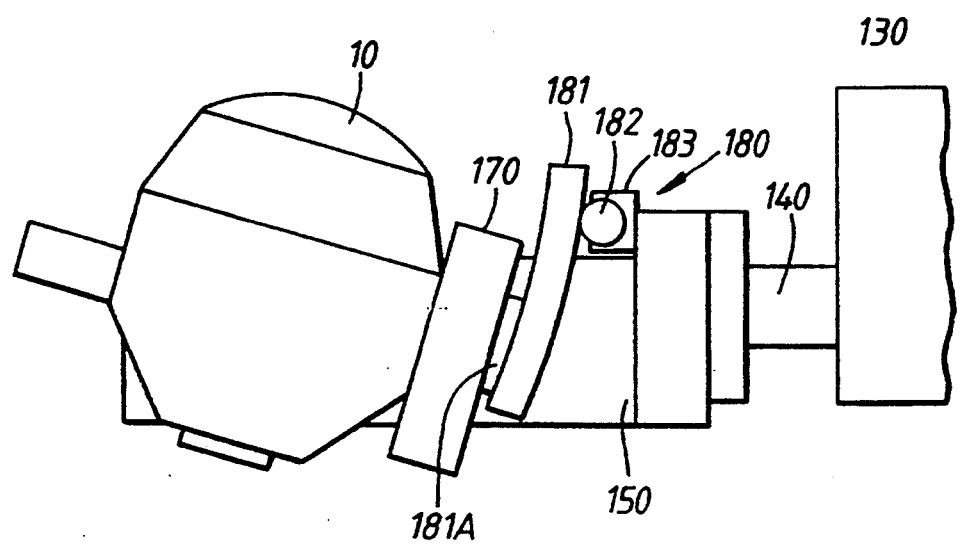
Figure 13:
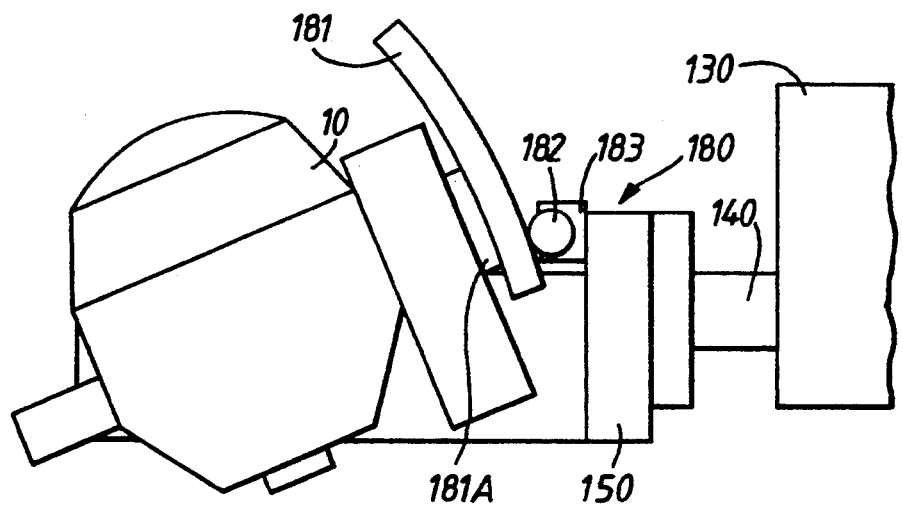

Referring back to FIGS. 11, 12 and 13, a base portion of the C-shaped arm 150 has an inclination mechanism 180. This inclination mechanism 180 consists of a curved rack gear 181 fixed to the applicator support base 170 by an attachment 181A, a pinion gear 182 for engaging with the curved rack gear 181, and a motor 183 for rotating the pinion gear 182. In the above construction, when the motor 183 is energized based on the control signal from the second switch 35 b, then the curved rack gear 181 is slided in an up or down direction. Consequently, the applicator 10 integrated with the C-shaped support 160 is inclined as shown in FIG. 11 to FIG. 13.

Referring to FIG. 10, a grip 190 is fixed to the arm portion of the C-shaped arm 150. By means of the grip 190 the applicator 10 permits getting the best suited position for treatment operation and turn over between the downward approach and the upward approach by hand-powered operation.

Figure 14:
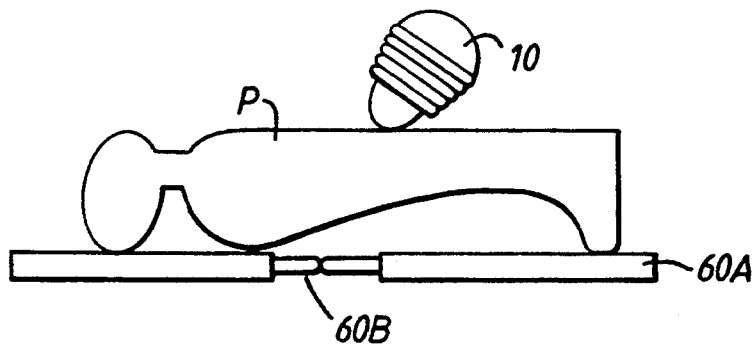
Figure 15:
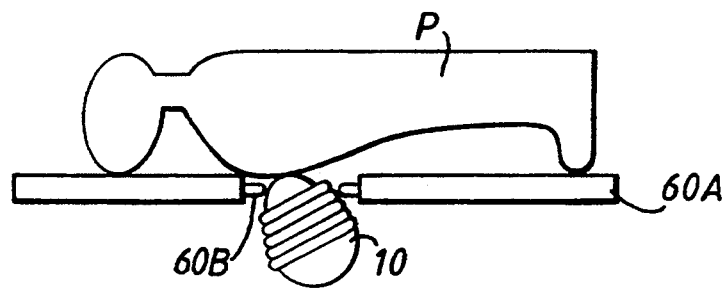

As described above, according to the present embodiment, the operator can select either the downward approach or the upward approach. Moreover, the operator can easily operate the apparatus to coincide the focus point of the shock wave to the calculus in both the downward and upward approaches. Hence, as shown in FIG. 14 and FIG. 15, this shock wave treatment apparatus is very convenient for treatment operation of both gallstones and kidney stones. In this case, when the downward approach is selected, then the shutting and opening portion 60B is shut, and when the upward approach is selected, then the shutting and opening portion 60B is opened. Then, the selection of which of the downward and the upward approaches is achieved by controlling the arm rotation mechanism 144 within the sliding member 130. The operator can supply a command to the CPU 33 for moving the applicator in several directions, i.e. horizontal (XY-axis), large up and down (large Z-axis), small up and down (small z-axis), turn over, and inclination movement. Then, the command from the CPU supplied to the motor corresponds to the command provided to the fixed operation panel 34 or the operation panel 35 which can easily be turned on or off by the operator. By the way, this operation panel 35 is removed when the applicator 10 is turned over from the downward to upward approach. After that, the operation panel 35 is fitted on the applicator 10 again. When the approach direction of the applicator 10 is changed, then the movement direction instructed by the operation panel 35 regarding small z-axis and rotation movement is reversed compared with an indication arrow on the operation panel 35. However, in this invention, this reversed movement regarding small z-axis and rotation movement can be prevented by a feature of the inverter circuit IN 1 and IN 2 shown in FIG. 3. Namely, when the approach direction is changed from downward to upward, the switch 70A and 70B within the motor control unit 70 is switched to a side of the inverter circuit IN 1 and IN 2, respectively, based on the output signal of the approach direction detector 149. According to the above switching, the control signal from the switches 35 a and 35d within the operation panel 35 is inverted by the inverter circuit IN 1 and IN 2, respectively. Hence, although the approach direction of the applicator is turned over, the operator can operate along the arrow indicated on the operation panel 35.

Moreover, the operation panel 35 allows one to operate the applicator for positioning using remote control from a detached area.

Figure 16:
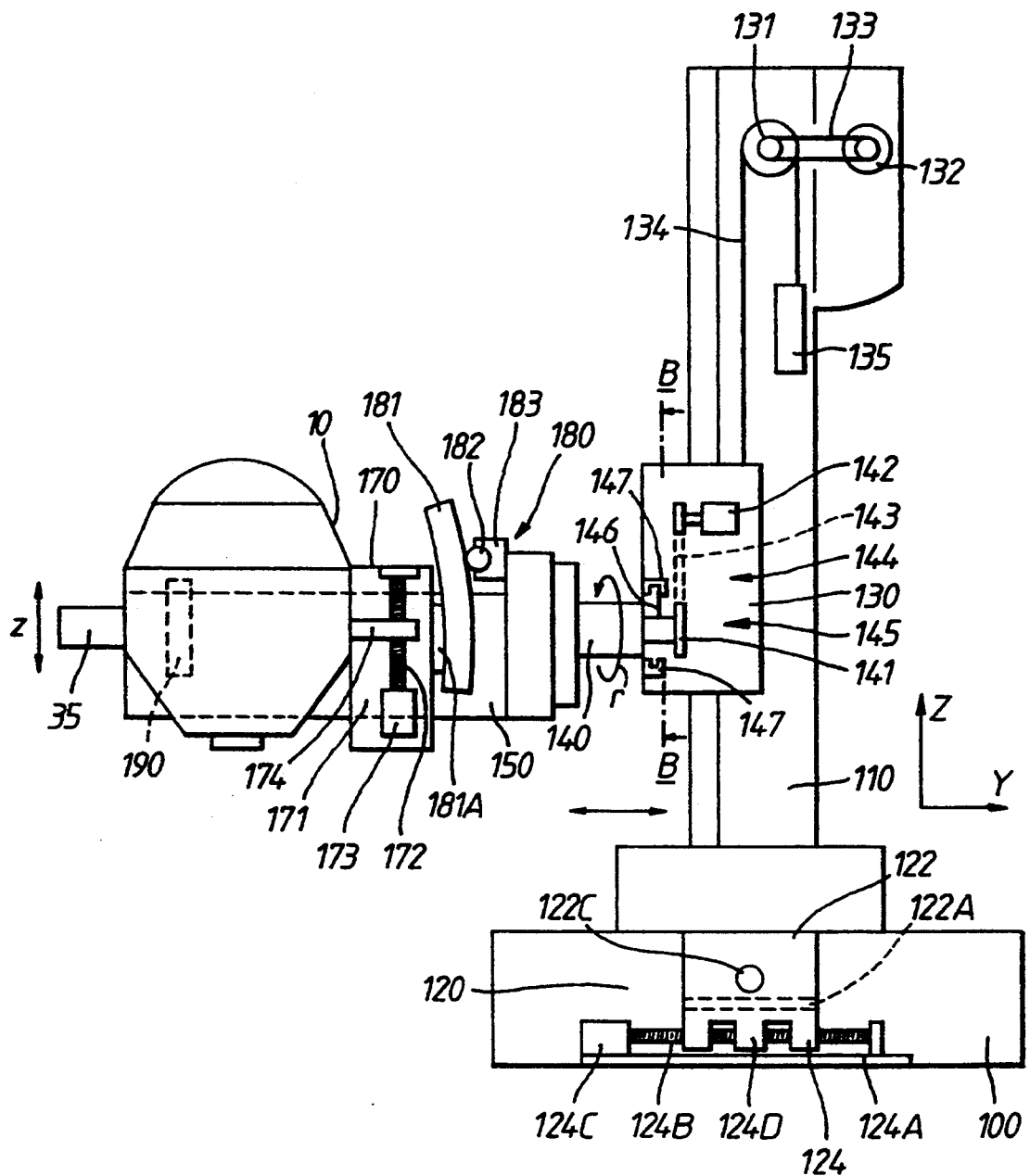
FIG. 16 is a variation of FIG. 10.
Figure 17:
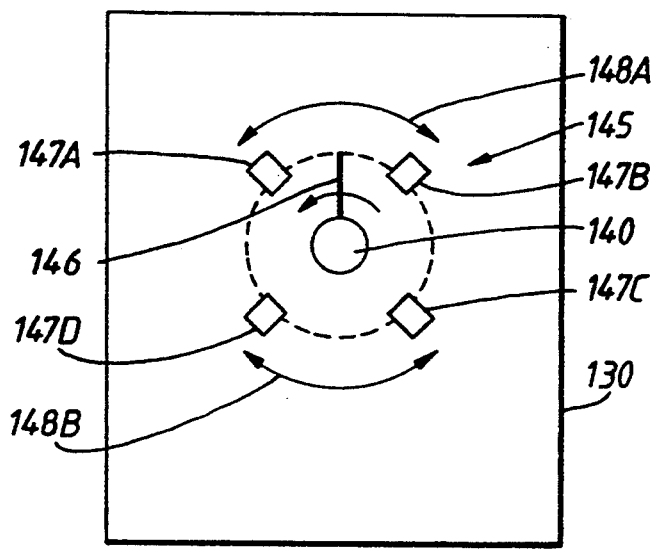
FIG. 17 is a partial sectional view of an approach direction device shown in FIG. 16.

A second embodiment will be described below, referring to FIG. 16 and FIG. 17. The second embodiment has a function that displays a B-mode image on the monitor 42 and is turned over automatically based on the approach condition in the downward or the upward approach. Namely, as shown in FIG. 16, rotation position detecting device 145 is provided within the sliding member 130. This rotation position detecting device 145 comprises a rod 146 fixed to the rotating axis 140 and four sensors 147A, 147B, 147C, and 147D for detecting a position of the rod 146. The sensors 147A to 147D are arranged along a locus of the rotated rod 146 at an equal spacing with respect to each other for detecting the position of the rod 146 rotated integrally with the rotating axis 140. The output of the sensors 147A to 147D is supplied to an approach direction detector 149 shown in FIG. 3. This approach direction detector 149 judges whether the applicator 10 is in the downward approach or is in the upward approach based on the output of the sensors 147A to 147D indicating the position of the rod 146. As shown in the FIG. 17, when the rod 146 is in an area 148A between the sensors 147A and 147B, then the approach direction detector 149 judges a downward approach condition, and when the rod 146 is in an area 148B between the sensors 147C and 147D, then the approach direction detector 149 judges an upward approach condition.

Also, a judgement signal of the approach condition obtained from the approach direction detector 149 is supplied to the CPU 33 via the applicator 20. The CPU 33 supplies a control signal to the B-mode control device 41 via the switching unit 43 for setting the displayed condition of the B-mode image displayed on the monitor 42 based on the judgement signal of the approach condition.

Figure 18:
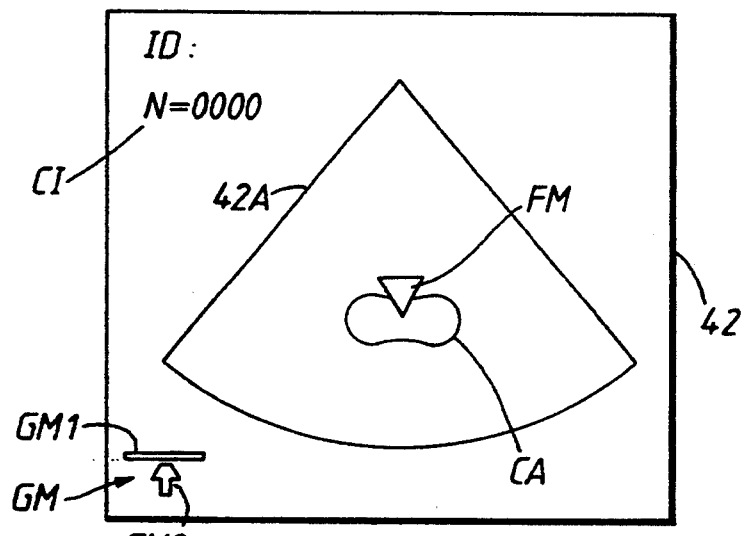
FIG. 18 illustrates a condition of the upward approach displayed on a monitor shown in FIG. 3.

This B-mode control device 41 is connected with a switch unit 43 which can be changed manually between the AUTO position and the MANUAL position. When the AUTO position is selected, then the displayed condition is changed by the control signal regarding the approach condition from the CPU 33. For example, when the applicator is in the downward condition, the sector tomographic image is displayed on the monitor as shown in FIG. 5, and when the applicator is in the upward condition, the sector tomographic image is displayed upside down on the monitor 42 as shown in FIG. 6. On the other hand, when the contact of manual is selected, then the displayed condition is changed based on an instruct signal from a turn over setting switch 44. As another way of the indication of the approach condition, graphical marker GM also can be displayed in a side corner position of the monitor 42 as shown in FIG. 18. Here, a bar mark GM1 shows the couch, and an arrow mark GM2 shows the approach direction of the applicator 10. Hence, the graphical marker GM shows the upward approach. When the MANUAL position is selected, there is no relation between the approach condition and the display condition on the monitor 42. In this state, the display condition on the monitor 42 is only changed based on the instruct signal from a turn over setting switch 44.

In the above embodiment related to the shock wave treatment apparatus, this invention also can be provided to a hyperthermia apparatus by way of switching from the shock wave generator to a continuous ultrasonic generator.

Figure 19:
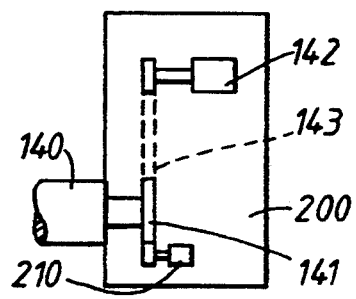
FIG. 19 is a variation of FIG. 17.
Figure 20A:
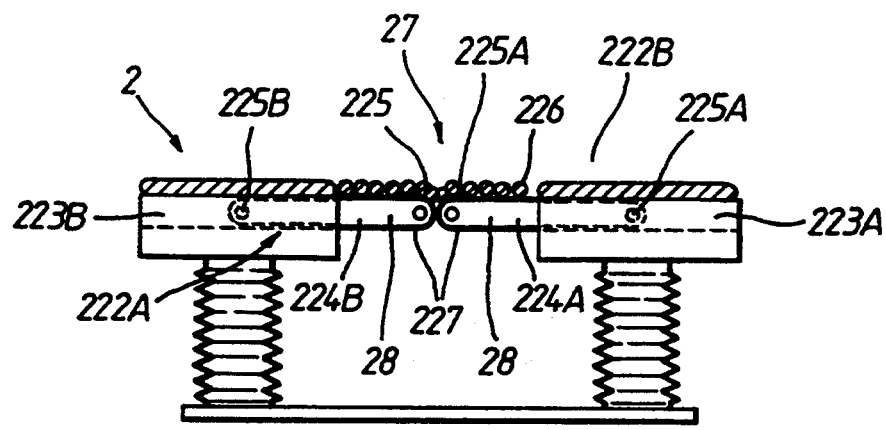
FIGS. 20a-b illustrate a preferred embodiment of a couch for a patient as shown in FIG. 1.
Figure 20B:
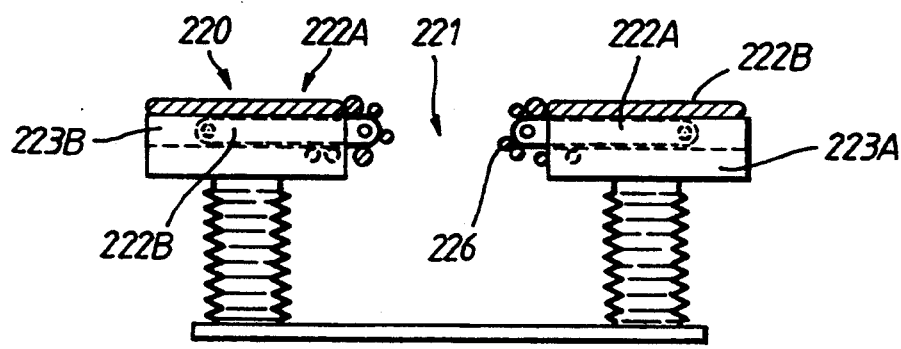
Figure 21:
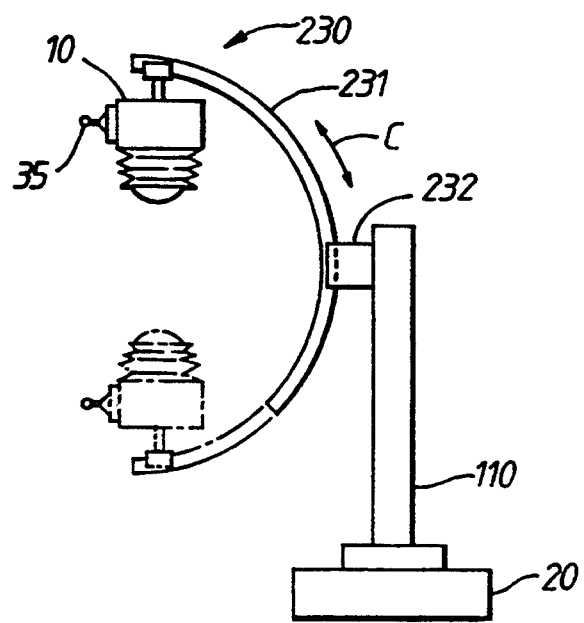
FIG. 21 is a variation of the applicator support device shown in FIG. 1.

The present invention is not limited to the above embodiment, and various other changes and modifications may be made within the spirit and scope of the invention. For example, the rotation position detecting device 145 can be modified as rotation position detecting device 200 as shown in FIG. 19. The gist of this construction is that a potentiometer 210 is provided in substitution for the rod 146 and detectors 147A to 147D. And, the couch 60 can be modified as couch 220 shown in FIG. 20 (a) and (b), namely, an opening 221 with a slide table 222A and 222B which can be slided along the longitudinal axis of the couch 220. The slide tables 222A and 222B are received in receiving spaces 223A and 223B. Further, the slide table 222A and 222B constructed with base 224A and 224B have rollers 225A and 225B provided on ends of the base 224A and 224B, belt 226A and 226B hanging between the both rollers 225A and 225B, and a plurality of cushion members 227 on belt 226A and 226B, hence the slide table 222A and 222B can be slided horizontally without rubbing the cushion members 227 on the patient. Furthermore, the applicator support device 20 can be modified to a J-shaped support arm 230 which supports the applicator 10 at an end portion thereto. This J-shaped support arm 230 is supported by an axis 232, around the axis 232 and slidably along an arrow C. In this embodiment, when the operator desires to turn over the applicator, then the i-shaped support arm 230 is rotated around the axis 232.

In the apparatus of this invention, the operator can select between the downward and the upward approach of the applicator 20 suitably, and this approach condition can be observed by the monitor which displays the approach condition. Consequently, the operator selects the downward approach when the object to be treated is a kidney stone, and the operator selects the upward approach when the object to be treated is a gallstone, and these selected approaches can be observed by the monitor. Also, the control signal from the switches 35 a and 35d within the operation panel 35 is inverted by the inverter circuit IN 1 and IN 2, respectively. Hence, although the approach direction of the applicator is turned over, the movement direction is not inverted. So the operator can operate along the arrow indicated on the operation panel 35 without relation to the downward and upward approach of the applicator. Furthermore, according to an embodiment described above, if the operator selects any approach direction, the ultrasonic treatment apparatus of the present invention effectively maintains proper positioning of the applicator.

We claim:
1. An ultrasonic treatment apparatus comprising:
an applicator including means for generating an ultrasound treatment wave for an object to be treated;
an ultrasonic probe arranged in the applicator and includes means for acquiring tomographic image information of the object;
an applicator support assembly supporting the applicator such that the applicator is movable in several directions;
means for changing an approach direction of the applicator between a downward approach and an upward approach against the object in order to achieve suitable treatment of the object to be treated;
monitor means for displaying the tomographic image information of the object supplied from the ultrasonic probe;
approach direction indicating means for indicating a condition of the approach direction of the applicator, the approach direction being either a downward approach or an upward approach with respect to the object on the monitor means; and
a turnover switch which is manually operated by an operator wherein said approach direction indicating means is controlled based on said turnover switch.

2. An ultrasonic treatment apparatus according to claim 1, wherein the applicator support assembly comprises a base fixed on a floor, an X-Y coordinate displace means connected to the base for displacing the applicator on a two-dimensional plane, a tower which is connected to the base, a Z direction displace means connected to the tower for displacing the applicator perpendicular to the two-dimensional plane, an arm member having a rotation axis which is supported by the tower along the rotation axis, and a rotation means for rotating the applicator around an axis horizontally arranged along the two-dimensional plane.

* * * * *